(12) United States Patent
Vandamme et al.

(10) Patent No.: US 6,627,235 B2
(45) Date of Patent: Sep. 30, 2003

(54) PROCESS FOR OBTAINING IMPROVED STRUCTURE BUILD-UP OF BAKED PRODUCTS

(75) Inventors: Erik Jerome Vandamme, Gent (BE); Christian Emile Florius G. Renard, Waver (BE); Filip Remi Jules Arnaut, Roosdaal (BE); Nicole Melanie Francine Vekemans, Herselt-Blauberg (BE); Pierre Patrick Aldo Tossut, Fleron (BE)

(73) Assignee: Puratos N.V. (BE)

( * ) Notice: Subject to any disclaimer, the term of this patent is extended or adjusted under 35 U.S.C. 154(b) by 0 days.

(21) Appl. No.: 10/162,955

(22) Filed: Jun. 3, 2002

(65) Prior Publication Data

US 2003/0039722 A1 Feb. 27, 2003

Related U.S. Application Data

(63) Continuation of application No. 09/273,404, filed on Mar. 22, 1999, now Pat. No. 6,399,119, which is a continuation of application No. 08/802,196, filed on Feb. 14, 1997, now abandoned.

(30) Foreign Application Priority Data

Feb. 15, 1996 (BE) .............................................. 9600136

(51) Int. Cl.⁷ ................................................. A21D 2/18
(52) U.S. Cl. .............................. 426/18; 426/20; 426/94; 426/496; 426/658
(58) Field of Search ................................ 426/549, 658, 426/94, 18, 20, 496

(56) References Cited

U.S. PATENT DOCUMENTS 2,983,613 A  5/1961  Bohn

FOREIGN PATENT DOCUMENTS

EP   0 153 013 A2   8/1985
WO   WO 91/07106    5/1991

OTHER PUBLICATIONS

Jeanes, A, et al. (1954), *Characterization and Classification of Dextrans from Ninety–Six Strains of Bacteria*. J. Am. Chem. Soc., 76:5041–5052.

Ross, A. S. (1995). Thesis, University of New South Wales, Australia. Accession No. AAI0576448. XP000610156. *Adding Dextrans (1 to 6–alpha–d–glucans) to Wheat Flour; Effects on Flour Components, Dough Rheology and End–Product Quality*. Dissertation Abstracts International, 56–07(B):3524.

Gvozdyak, et al. (1992). *Production of Baked Articles from Dough Containing No Yeast—Involves Mixing Flour with Hetero–polysaccharide Produced by Xanthomonas Campestris Bacteria*. Derwent. XP0002032217 (Abstract enclosed).

*Primary Examiner*—Lien Tran
(74) *Attorney, Agent, or Firm*—Knobbe Martens Olson & Bear, LLP

(57) ABSTRACT

A process for obtaining improved structure build-up of baked products includes the steps of incorporating a sufficient amount of exopolysaccharides into a dough to show a rise in viscosity with time and thereafter maintaining the achieved viscosity. New dextrans and new micro-organisms producing them can be used in the process. Thus, the dough and baked products containing these dextrans are produced.

6 Claims, 5 Drawing Sheets

PROCESS FOR OBTAINING IMPROVED STRUCTURE BUILD-UP OF BAKED PRODUCTS

CROSS REFERENCE TO RELATED APPLICATIONS

This application is a continuation of U.S. patent application Ser. No. 09/273,404 filed on Mar. 22, 1999, now U.S. Pat. No. 6,399,119 B1 which is a continuation of U.S. patent application Ser. No. 08/802,196, filed Feb. 14, 1997, abandoned, which claims priority to Belgian Application BE 09600136, filed Feb. 15, 1996, the disclosures of which are herein incorporated by reference in their entireties.

FIELD OF THE INVENTION

This invention is related to a process for obtaining improved structure build-up of baked products as well as new dextrans and new micro-organisms producing them. The present invention is also related to dough and baked products containing these dextrans.

BACKGROUND OF THE INVENTION

The rheological properties of a dough are determinant for the quality of the baked end product. In order to estimate the quality of bread and baked products in general, the parameters listed hereafter are used: volume, crumb structure softness and shelf life, color of the crumb and the crust, flavor and shape (round, flat).

So called bread improvers are used to enhance the rheological properties of the dough and consequently, to obtain a better baked end product. For this purpose, chemical agents are used, such as: potassium bromate, ascorbic acid, iodates, azodicarbonamide, cysteine. Emulsifiers are used too, such as: diacetyltartaric acid esters, sodium and calcium stearoyllactylate, and if necessary sucrose-esters.

Some enzymes also improve the properties of the dough. The usage of α-amylases and xylanases is now widely spread. There are also oxidases and peroxidases which have a marginal, improving influence on the rheology of the dough, but this does not always means a better end product.

The use of polysaccharides as bread improvers is known and documented. The positive effect on dough rheology and on the total bread quality is always limited to specific cases or to combinations with other additives or ingredients. In most cases, guar gum is used, or locust bean gum, and if necessary carrageen or alginates (Ward F., 1993).

In practice, it is always by combining several of the above mentioned components that a commercial bread improver is created. The formulation of such a bread improver is adapted, according to the type of the end product, bread, rolls, or "Belgian pistolet", "French baguette", or according to the applied process: direct processing, retarded fermentation, deep frozen dough.

Although the possible combinations are endless, it is clear that the current additives and ingredients do not always meet the strict requirements of the modern bakery technology. Moreover, the use of certain additives is limited or prohibited by law. For instance, the use of bromate is forbidden in Europe, whereas it is limited in the U.S., on a voluntary basis. New ingredients which can replace existing chemical additives, or which have a new function, besides the currently existing additives are still being researched. Especially when they are based on natural products.

The ingredients mentioned above, and the additives for breads and rolls, are also used in pastry products. (cake, biscuit). In these pastry products, the volume of the baked end product is also one of the quality criteria besides, amongst others, softness and shelf life.

STATE OF THE ART

The use of dextrans in the field of bakery is not widely spread, although a number of applications have been described. The addition of dextrans in wheat doughs and the negative influence of this addition on the end quality of baked bread is known (Ross A. S. et al., J. Sci. Food Agric. 1992, 91–98; Ross A. S.: PhD Thesis, University of New South Wales (Australia), 1994 (XP000610156) & Dissertation Abstracts International, part 56, Nr. 7, p. 3524, 1996).

On the other hand, the Japanese patent application JP-07055124B2, the positive influence of dextrans on the softness and the shelf life of baked products has been proved. In addition, dextrans seem to have a small influence on the gassing power by yeast. This influence is comparable to other components such as locust bean gum, arabic gum, egg white, gelatine (Kolostori M., Elelmezesi Ipar 1978, 32(3), 107–112).

The U.S. Pat. No. 2,983,613 describes incorporating into the dough an amount of dextrans sufficient to soften the gluten content of the dough and to increase the specific volume of the resultant bakery product. This document describes that the bread which contains dextrans was about 20% greater in volume than products which do not contain dextrans.

Said dextrans are prepared by growing the microorganism *Leuconostoc mesenteroides* B512, resulting in dextrans having a molecular weight from about $2 \times 10^6$ to about $4 \times 10^6$ dalton.

Dextrans have been described in EP-0153 013-A as bulking agent in formulations, suitable for enteral administration to man. This is mainly for diet reasons (low calorie) and for the treatment of a condition of the gastrointestinal tract in a human.

Dextrans can be synthesized by bacteria. Dextrans are α-D-glucans, which are mainly composed of (1–6) linked α-D-glucopyranosyl residues) They are mainly produced by bacteria which grow on a substrate, the only source of carbon being sucrose. These bacteria mainly belong to the group of lactic acid bacteria, and more specifically to the species of the Lactobacillus, Leuconostoc and Streptococcus. Examples of the producers of dextrans are to be found in the table below.

| Lactobacillus | Leuconostoc | Streptococcus |
| --- | --- | --- |
| L. acidophilus | L. dextranicum | S. bovis |
| L. brevis | L. mesenteroides | S. challis |
| L. casei | L. citreus | S. faecalis |
| L. pastorianus | | S. mitis |
| L. confusus | | S. mutans |
| L. sanfrancisco | | S. sanguis |
| L. viridiscens | | S. viridans |

Purified dextrans are generally obtained by deproteinization of polysaccharides, which are isolated from the fermentation fluids.

Further purification is obtained by fractionated precipitation with alcohol or ketones. Dextrans which have a well defined molecular weight are obtained by partial hydrolysis.

The structure (such as length of the chain, degree of branching, type of links) of the dextrans are mainly defined by the bacteria subspecies, and less by the family, the genus, or the species. Some of the bacteria produced soluble and insoluble dextrans at the same time.

The basic structure of dextrans are (1–6) linked α-D-glucopyranosyl residues. Sometimes, there are branchings at C-2, C-3, or C-4. Isolated (1–3) linked α-D-glucopyranosyl residues or sequences of these residues can interrupt the (1–6) regions. All of the dextrans are more or less ramified, and the branching very much depends on the subspecies (Jeans A. et al., J. Am. Chem. Soc., 1954, 76, 5041–5052). Most of the branchings are composed of single α-D-glucopyranosyl residues, although branchings have been found with 2–50 monomers. Some branchings are formed by (1–3) linked α-D-glucopyranosyl residues.

Alternane is composed of glucose entities, which are alternately α(1–6)-linked and α(1–3) linked. It is amongst others produced by Leuconostoc mesenteroides NRRL B-1355.

Soluble dextrans are composed of sequences of (1–6) linked α-D-glucopyranosyl residues, on which, at irregular intervals, branchings of single α-D-glucopyranosyl residues are substituted.

Insoluble dextrans are more complex and they often contain more (1–3) linked α-D-glucopyranosyl sequences.

Dextrans are synthesized by dextransucrase (E.C.2.4.1.5). The IUPAC name is sucrose: 1,6-α-D-glucan 6-α-D-glucosyltransferase (IUB, 1984). The enzyme is most frequently extracellular, and is induced by sucrose. The pH-optimum for the Leuconostoc dextransucrase lies between the pH 5.0 and pH 5.5 at the temperature of 29–34° C.

A procedure for the production and the isolation of dextransucrase of Leuconostoc mesenteroides is described by Ajongwen N. J. (Biotechnol. Lett., 1993, 9(4), 243–248).

Dextrans can also be synthesized by means of dextrine dextranase (E.C. 2.4.1.2) of for instance Acetobacter capsulatus ATCC 11894 Kazuya Yamamoto (Biosci., Biotech, Biochem. 1993, 57(9), 1450–1453).

The chain length of the dextrans depends on the conditions of fermentation. This means that the presence of acceptors such as maltose will influence molecular weight.

Dextrans form viscous solutions. These solutions show a Newtonian behavior when concentrations <30% w/w for low molecular weight dextrans. Dextrans with a higher molecular weight show a slightly pseudoplastic behavior when concentrations >1.5% w/w (McCurdy R. D., 1994) There are no single correlations between the viscosity of dextrans solution and its branchings. The viscosity enhancing effect is due to a combination of structure (more or less branched) and molecular weight (Jeanes A. et al., J. Am. Chem. Soc., 1954, 76, 5041–5052).

SUMMARY OF THE INVENTION

The present invention is related to a process for obtaining improved structure build-up of baked products comprising the step of incorporating into a dough a sufficient amount of exopolysaccharides, said exopolysaccharides showing in a solution a rise in viscosity (when subjected to a constant stress) with time and showing thereafter the maintain of the achieved viscosity. Preferably, said rise in viscosity is higher than $0.4 \times 10^{-3}$ Pas preferably higher than $0.8 \times 10^{-3}$ Pas after 5,000 seconds for a 1% solution by weight of exopolysaccharides under stress of 0.5 pa. Therefore, the inventors noticed that said exopolysaccharides surprisingly are capable of a considerable increase of the specific volume of a baked product. Advantageously, said expolysaccharides, preferably dextrans, are obtained from bacteria belonging to the group of lactic acid bacteria. Mainly dextrans with a high molecular weight ($>2 \times 10^6$ dalton) and few branching seem to have the most marked effect. In many cases, such dextrans also give very viscous solutions. The effect is not merely due to viscosity as such, because xanthan does not have the same effect and still it forms very viscous solutions. Guar also gives viscous solutions and has a bad and limited effect on the bread volume. Slightly ramified dextrans with a low viscosity but with a high molecular weight have also been tested. The positive effect of the dextrans of the leuconostoc mesenteroides subspecies especially the strain LMGP 16878 (hereafter called P-171) is mostly pronounced (p-171). The dextrans are preferably composed of linear chains with a high molecular weight. Dextrans with a high molecular weight and more branchings are less efficient, as proven by the dextrans of Lactobacillus sanfrancisco P-172 and Leuconostoc mesenteroides B512F as described hereafter. Linear dextrans with a low molecular weight are also less efficient. The molecular weight and the degree of branching depend on the subspecies and the conditions of fermentation (sucrose concentration, temperature).

The present invention is also related to new dextrans exceeding $2 \times 10^6$ dalton and having a branching grade lower than 5%. Preferably, said dextrans are also characterized by the 1H-NMR spectra as represented in the enclosed FIG. 2. Preferably, said dextrans are lyophilized. Another aspect of the present invention is related to a micro-organism producing the dextrans according to the invention and having preferably the deposit number LMGP-16878. A last aspect of the present invention is related the dough and the baked food products comprising the dextrans according to the invention such as bread, "Belgian pistolets", deep frozen dough, cake, sponge cake, etc.

The subspecies Leuconostoc mesenteroides of the invention was deposited according to the Budapest Treaty in the Belgian Coordinated Collection of Micro-Organisms (BCCM) under the number LMGP-16878.

SHORT DESCRIPTION OF THE DRAWINGS

DESCRIPTION OF THE PREFERRED EMBODIMENT OF THE INVENTION

1. Structure Characterization of Leuconostoc mesenteroides Species Dextrans Through Proton-Nuclear Magnetic Resonance Spectrometry (1H-NMR)

Dextran-fractions were obtained from Leuconostoc mesenteroides subspecies NRRL B512F, Leuconostoc mesenteroides P-171 (to be found in the BCCM under the number LMGP-16878) and Lactobacillus sanfrancisco P-172. Dextran was isolated using the methods well-known by a man skilled in the art described hereafter. 1H-NMR spectra of the obtained dextran fraction was been registered on a Bruker AM-300 (300 MHz) machine at the temperature of 85° C. The samples had previously been dissolved in $D_2O$ (1 mg/ml) lyophilized and dissolved again in $D_2O$. Acetone was used as a standard (2.23 ppm).

Figure 1:
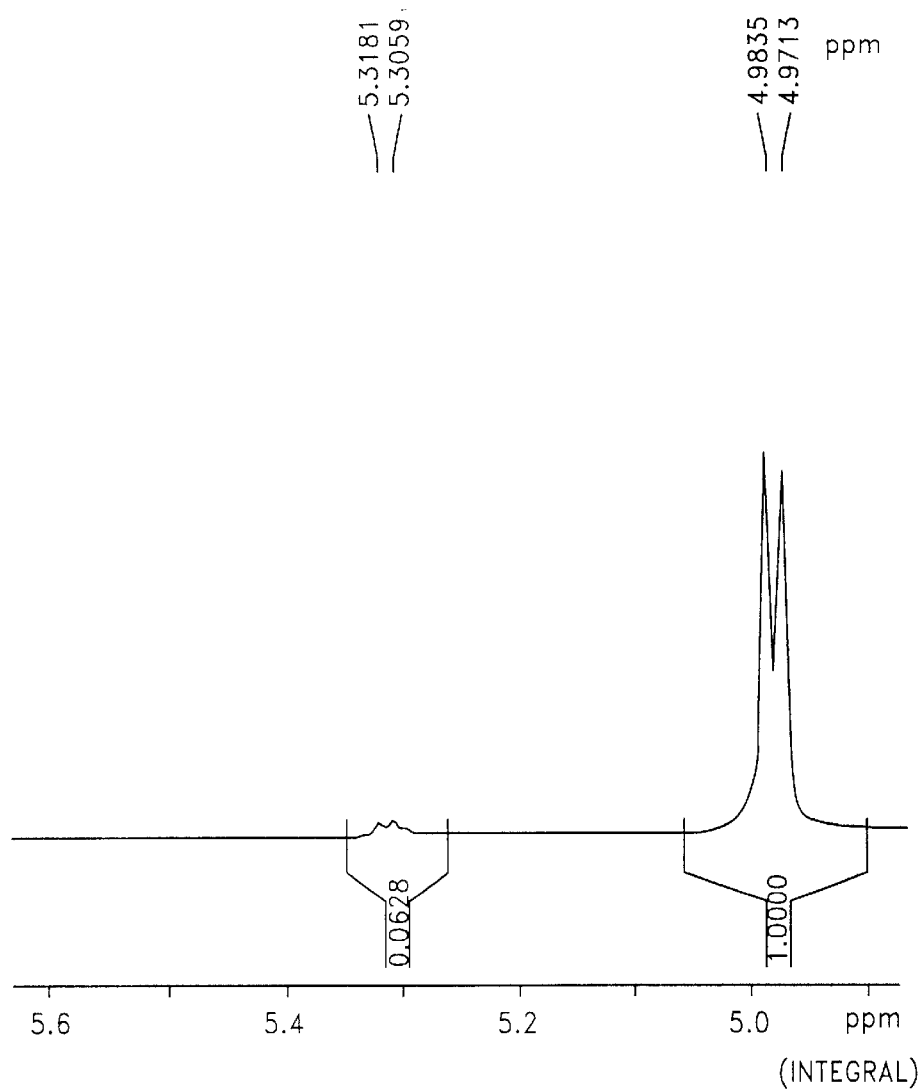
FIG. 1 represents the 1 H-NMR-spectrum of the dextrans fraction 'B512F'
Figure 2:
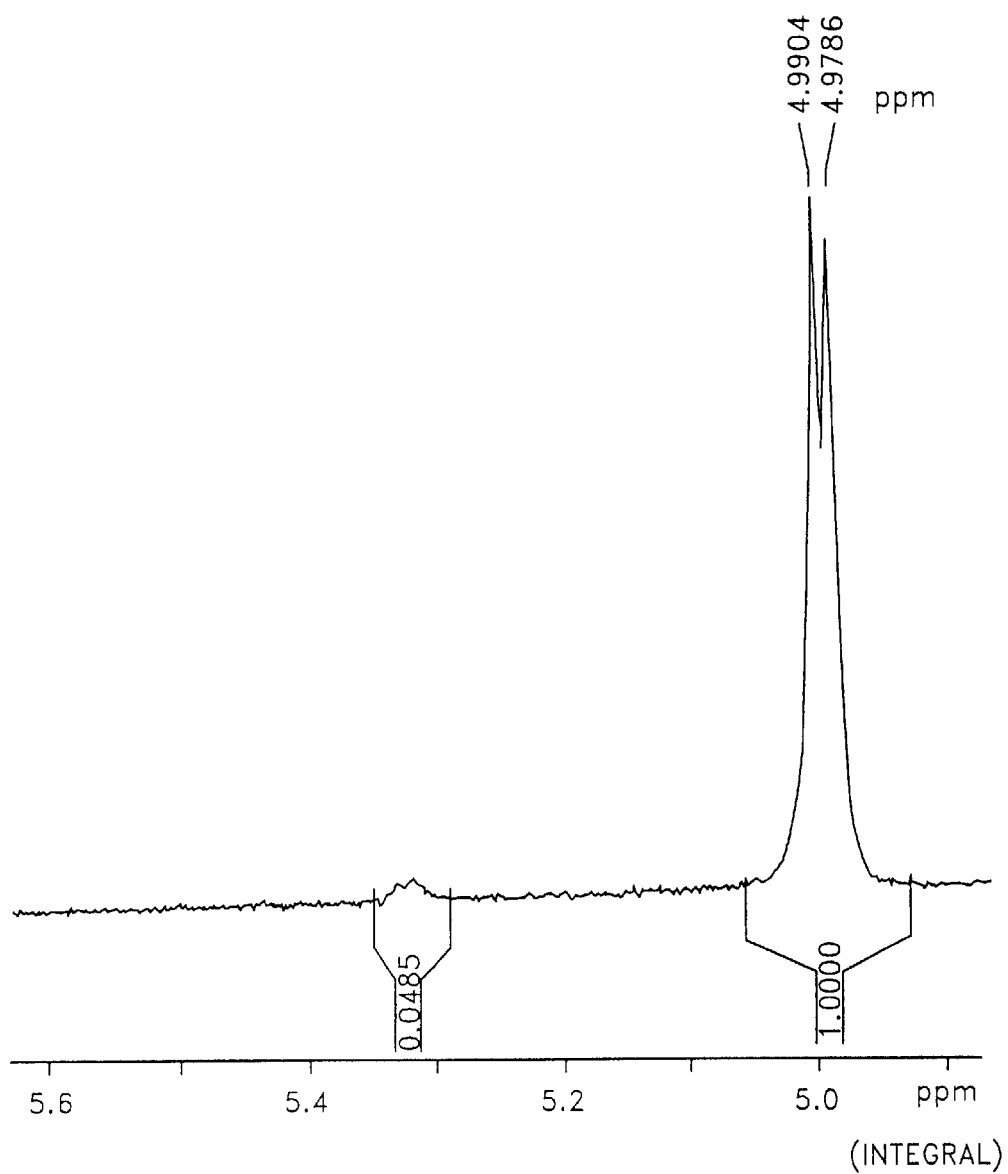
FIG. 2 represents the 1 H-NMR spectrum of the dextrans fraction 'P171'
Figure 3:
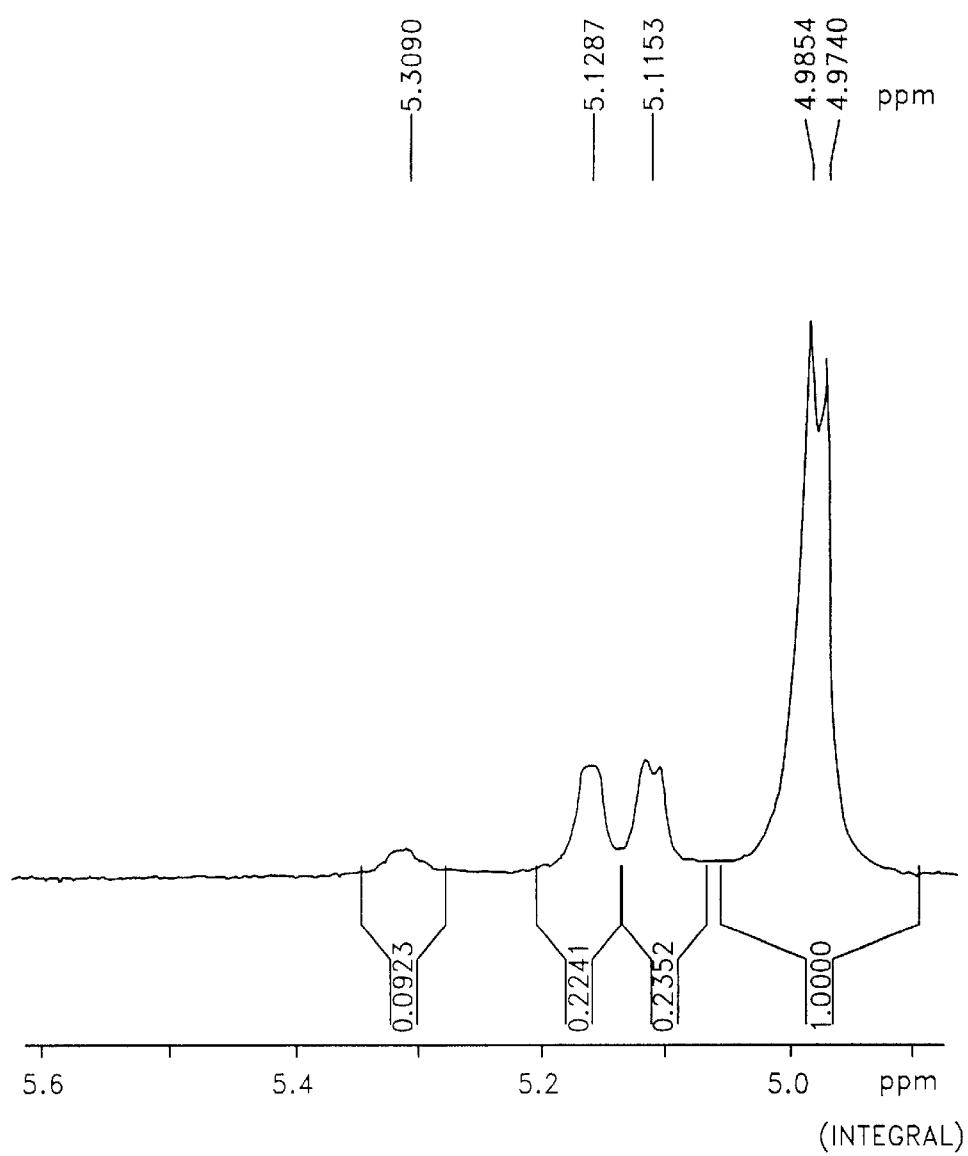
FIG. 3 represents the 1 H-NMR-spectrum of the dextrans fraction 'P172'

The 1H-NMR of the dextran fraction B512F, p-171, and p-172 are represented in the enclosed FIGS. 1 to 3.

For the three dextrans samples, a clearly pronounced duplet was detected in the anomeric area at δ4.99 ppm and δ4.97 ppm. Pasika W. M. and Gragg L. H. (Canadian Journal of Chemistry, 1962, 41,293–299) assign the duplet with the greatest intensity and δ5.05 ppm in the spectrum of the linear dextran NRRL B-512F, to the anomeric protons of the α(1–6) linked glucose monomerics. Dextran NRRL B-512F are for 95% composed of α-(1–6)-and for 5% of α-(1–3)-linked glucose monomers (Robyt, J. F., 1992, Developments in carbohydrate chemistry, ed. Alexander R. J. AACC St. Paul, Minn., 55121-2097, USA). Anomeric protons of the α(1–3) linked glucose monomers cannot be detected by Pasika and Gragg (1962), with the help of a 60 MHz spectrometer. According to these authors, anomeric protons of α-(1–3)-linked glucose-monomers in the spectrum of the branched dextrans B-742 are characterized by a resonance at δ5.40 ppm. Robyt (1992) reports the presence of 50% of α-(1–6)—and 50% of α(1–3) linked glucose monomers, for these branched dextrans of Leuconostoc mesenteroides B-742. In the spectrum of the branched dextrans, Pasika and Gragg (1962) detect two additional resonances at δ5.29 ppm and δ4.67 ppm. The authors assign these peaks respectively to α- and β-configuration of the anomeric protons of the reducing ends of the dextran-polymers. For linear dextrans, the concentration of anomeric protons is smaller than the detection limit of the spectrometer.

Seymour et al (Carbohydrate Research, 1979, 74, 77–92) describe the 1H-NMR-spectra, registered with a 100 MHz spectrometer at 90° C., of dextran-fractions of NRRL sub-species of Leuconostoc mesenteroides B-742, B-1299, B-1355 and B-1501, as well as the native dextrans of L. mesenteroides B-1142, B-1191, B-1402. Based on these spectra, the authors attribute the resonance with δ4.93–4.87 ppm to the anomeric protons of the chain extending α-(1–6)-linked glucose-monomers. Peaks at δ5.03–5.08 ppm are attributed to the anomeric protons of 2,6-di-O-substituted α-D-glucopyranosyl residues, whereas the peaks with δ5.22–5.27 ppm are assigned to the anomeric protons of 3,6- and 4,6-di-O-substituted α-D-glucopyranosyl residues. Based on these data, and the 1H-NMR-spectrum of the dextrans sample B512F, it was possible to attribute the doublet with δ5.31–5.30 ppm, present in the spectra of the three dextrans samples, to the anomeric protons of the α-(1–3) linked glucose-monomers. The small differences in the delta values measured can be explained by a lower temperature at which the spectra have been registered. Seymour et al. have indeed shown that a reduction of the temperature at which the spectrum is registered causes a small shift towards higher ppm-values. When comparing the intensities of the peaks with δ4.98–4.97 and δ5.31–5.30 ppm in the spectrum of the dextrans fraction, originating from the Leuconostoc mesenteroides B-512F, the inventors note that 94% of α(1–6)-linked glucose-monomers and 6% of α-(1–3)-linked glucose-monomers.

Meyer and Lamberts (Carbohydrate Research, 1978, 66,33–42) distinguish doublets of anomeric protons of homogenous and heterogeneous α-(1–6) and α-(1–3)-linked glucose-monomers, in the 1H-NMR-spectra of Streptococcus mutant dextrans. The spectra were registered at the temperature of 80° C. in a 9:1 $Me_2SO$-d6-$D_2O$ mixture. For this reason, it is difficult to compare these spectra to those registered in $D_2O$.

In the zone of the not α-(1–6) resonances of a spectrum registered at 270 MHz, Meyer and Lamberts, note two duplets at δ5.00 and δ5.09 ppm. These are respectively attributed to the anomeric protons of heterogeneous and homogenous α-(1–3)-linked glucose residues. The authors also detect a major resonance with δ4.75 ppm, in the zone of α-(1–6) resonances, caused by the anomeric protons of homogenous α-(1–6) linked, chain prolonging glucose monomers, and a shoulder peak of heterogeneous α-(1–6) linked glucose residues.

This shoulder peak can also be detected in 1H-NMR spectrum registered at 300 MHz of the dextran-fraction B-512F. According to the data of Meyer and Lamberts (1978) and the known composition of this dextran fraction, it is possible to assign this shoulder peak to the 6% of α-(1–3)-linked glucose-monomers. In the zone of the α-(1–3)-linked glucose-monomers, the inventors detect a duplet with a small shoulder at slightly higher ppm-values. This points to the presence of a predominantly heterogeneous α-(1–3) linked glucose-residue, which corresponds to the structure of dextrans originating from Leuconostoc mesenteroides 512F, as described by Robyt (1992).

As a conclusion from the previous analysis, we can assign the resonances noted at δ4.98–4.97 ppm and δ5.32–5.30 ppm in the spectra of dextrans-fractions B-512F and 'P171' to the anomeric protons of respectively homogenous α-(1–6) and heterogeneous α-(1–3)-linked glucose monomers. Correspondingly, we can assign the resonances noted at δ4.98–4.97 and δ5.30 ppm in the spectrum of the dextrans-fraction 'P172' to, respectively, α-(1–6) and α-(1–3)-linked glucose monomers. It is possible that the intermediate resonances originate from anomeric protons of α-(1–2)-linked glucose residues (see table Table I).

TABLE 1

| Type | a-(1–6) | a-(1–3) | other |
|------|---------|---------|-------|
| P171 | 95.4 | 4.6 | 0 |
| P172 | 64.4 | 5.95 | 29.6 |
| B512F | 94.1 | 5.9 | 0 |

2. Monosaccharide Composition

Polysaccharides (more or less 5 mg) were submitted to a pre-hydrolysis with $H_2SO_4$ 12 M (250 µl) during one hour at room temperature, and after dilution to $H_2SO_4$ 1 M, the process of hydrolysing was continued during three hours in a boiling water bath.

The monosaccharides which were formed are derivatized to alditol-acetates: 1.00 ml of an internal-standard-solution 10 mg of allose in 100 ml of a 1:1 diluted saturated benzoic acid-solution) was added to the hydrolysed substrate.

The test tubes were cooled in ice water and 1 ml of 25% $NH_3$ was added. One drop of 2-octanol is added, in order to avoid excessive foaming, and 200 µl of a solution of sodiumborohydride in $NH_3$2N is added as well.

During 30 minutes, the test tubes were incubated in a water bath at the temperature of 40° C.

400 µl of glacial acetic acid was added to the solutions. The tubes are shaken well (vortex). A part of the resulting mixture (500 µl) was transferred to another test tube (50 ml), mixed with 500 µl of 1-methylimidazol and 5.0 ml of acetic anhydride. The mixtures were allowed to rest during 10 minutes. Ethanol (900 µl) was added and the mixtures are allowed to rest again during another 5 minutes. After adding 500 μl of a bromophenolblue solution (0.04%), the test tubes were put in ice water and 5.0 ml of a 7.5M KOH-solution was added. After 5 minutes, a new 5.0 ml KOH-solution (7.5M) was added, and the test tubes were shaken by turning them upside down. After phase separation, the colorless, organic phase was dried with anhydrous sodium sulphate and the alditolacetates which were present, were separated at 225° C. on a Supelco SP-2380 column (30 m, 0.32 mm ID, 0.20 μm film thickness) with a Chrompack gas chromatograph model CP9001, flame ionization detector model 901A. Peak surfaces were calculated with HP3396 Series 20 II Integrator.

The following Table II represents the monosaccharide composition of the dextrans-fraction 'P171'.

TABLE II

| Sample | P171 |
|---|---|
| Arabinose (%) | 0.00 |
| Xylose (%) | 0.00 |
| Mannose (%) | 2.54 |
| Galactose (%) | 0.04 |
| Glucose (%) | 97.42 |

The mannose is an artifact of the analysis method.

3. Molecular Weight Distribution on Sephacryl

Molecular weight distribution of dextrans solutions 10 mg/10 ml 0.3% NaCl) was defined through gelpermeation chromatography on a Sephacryl S-500 HR column (Pharmacia, dextrans separating capacity of 40 to 20.000 kDa, I×2.5 cm, flow=2.5 ml/minute). Fractions of 2.5 ml/minute were collected and 1 ml of each fraction was analyzed on the total carbohydrate content.

Results revealed the high molecular weight of P-171, P-172 as well as of B-512F. Yet the P-171 had a higher molecular weight (see FIG. 2).

4. Viscosity Measurements

The viscosity measurements were carried out with the help of a Brookfield viscometer (Stoughton, Mass., USA).

Results show that the P-171 had a much higher viscosity than the B512F or P172. Nevertheless, the B512F can still cause a volume increase, providing that the molecular weight of the formed dextrans is high enough.

The visco-elastic properties of 1% by weight aqueous solution of the dextrans B512F (FIG. 4), P-171 (FIGS. 5 and 7) and P-172 (FIG. 6) were analyzed by a Bohlin controlled stress dynamic rheometer.

The solution was poured into the analysis vessel with concentric cylinders, and the following conditions were applied:
Stress 0.5 Pa
delay time 45 s
integration time 0 s
resting time 150 s
temperature 5° C.
The analysis was performed in duplicate.

Figure 4:
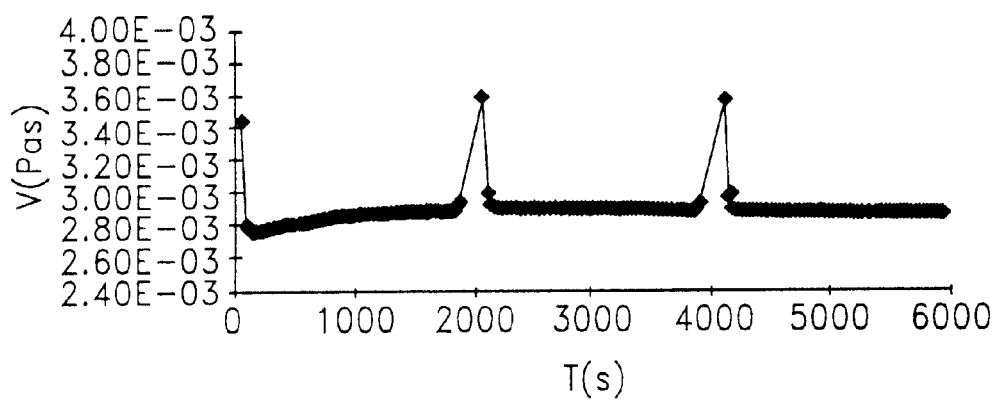
FIG. 4 represents the Viscosity profile of the dextrans fraction 'B512F'
Figure 5:
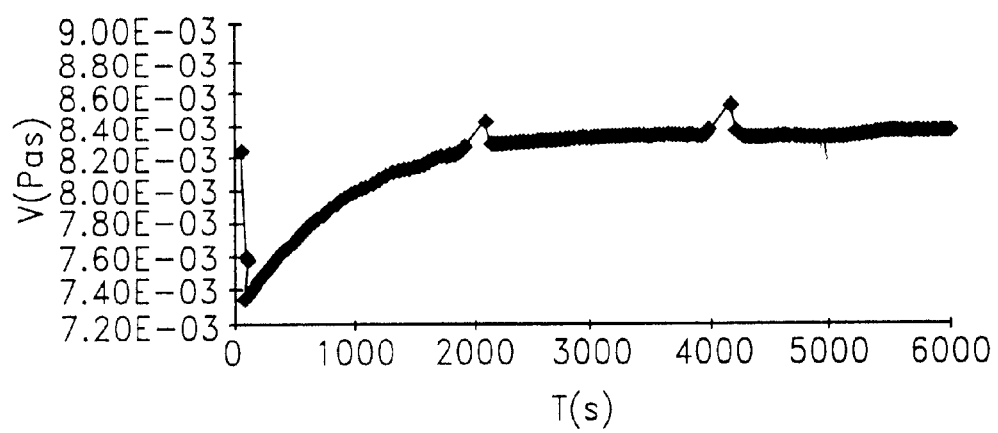
FIG. 5 represents the Viscosity profile of the dextrans fraction 'P171'
Figure 6:
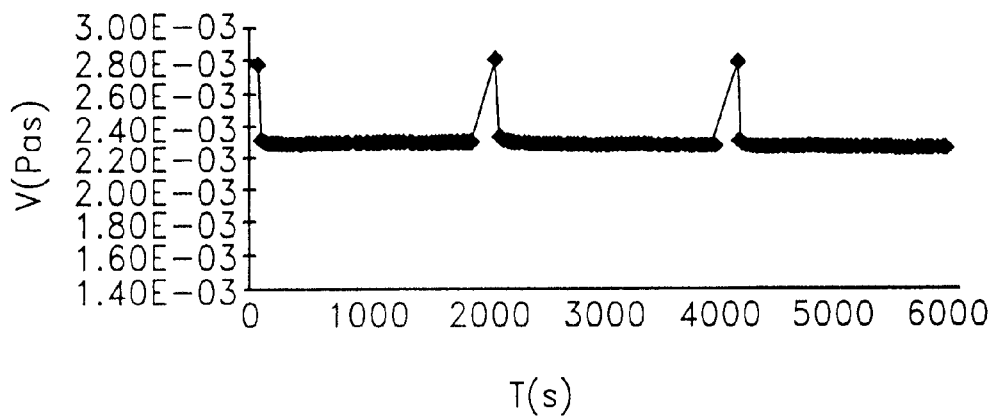
FIG. 6 represents the Viscosity profile of the dextrans fraction 'P172'
Figure 7:
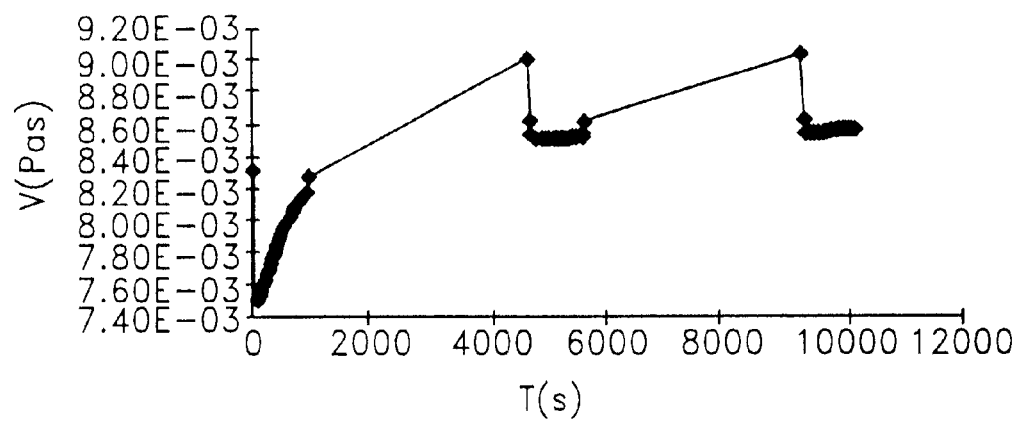
FIG. 7 represents the Viscosity profile of the dextrans fraction 'P171' with 36000 interruptions.

The FIGS. 4 to 6 clearly show a difference between the dextrans. Dextrans according to the invention (P-171) were building a structure when stress was applied. This was reflected by the increase of viscosity (expressed in Pas) with time. When stress application was halted (1), the build-up structure was retained even after an interruption of 3600 seconds (FIG. 7). Further application of stress had resulted in further building of structure. The rate of the increase of the viscosity was highest at the beginning of the application of stress.

Combined with the baking results, these data show a positive correlation between the ability to build a structure (increasing viscosity) under stress and a specific volume increasing effect of the dextrans in baked goods.

5. Results of the Baking Test 5.1 Protocol Baking Test 100 g of Bread

Ingredients:

| 100 g | wheat flour (Surbi Molens van Deinze) |
|---|---|
| 58 ml | water |
| 5% | fresh yeast (Bruggeman) |
| 2% | salt |
| 2% | crystalline dextrose |
| 4 mg | Vit C p.a. Sigma A7506 |

Recipe:
Mixing in a National pin kneader (National, Lincoln, Nebr., USA) until optimal mixing (+/−4.5 mn);
20 mn bulk fermentation at room temperature;
rounding up and allow to ferment for 20 mn at room temperature;
50 mn final proof in the bread forms at 36° C. and 80% of relative humidity;
Baking during 20 mn at 215° C. in the oven of National. The volume of the baked products was measured by the rapeseed displacement method, which is commonly used in the bakery sector. The baked products were evaluated on volume increase, compared to a reference.

Remark: Corrections were made for the water absorption of polysaccharides.

5.2 Protocol Baking Test 1 kg "Belgian Pistolets"

Ingredients:

| 1000 g | wheat flour Surbi (Molens van Deinze) |
|---|---|
| 610 g | water |
| 60 g | yeast (Bruggeman) |
| 20 g | salt |

Recipe:
13 mn mixing in an Artofex mixer;
Bulk fermentation (15 mn);
Afterwards the dough was refolded;
2nd Bulk fermentation (10 mn);
Intermediate proof 10 mn;
Rounding up with the help of a Rotamat (dough piece of 30 g);
Rest for 5 mn;
cutting of the dough pieces;
Final proof (80 mn);
Baking 20 mn at 230° C. in oven of the type Ooms, using steam.

Remark: Corrections were made for the water absorption of the polysaccharides.

5.3 Protocol Baking Test Sponge Cake (Pastry)

Ingredients:

| 500 g | Tegral Biscuit ® |
|---|---|
| 375 g | Whole eggs |
| 50 g | Water |

*Tegral Biscuit ® is a commercial product of Puratos N.V. Belgium. It contains a baking powder, emulsifier, cake flour and sugar.

Recipe:

All ingredients were mixed in a Hobart® mixer 15 to 30 seconds at speed 1 and 5 minutes at speed 3. After that the density of the batter was measured by filling and weighing a cup of which the volume is known.

200 g of batter was put in the baking pan (round, diameter 20 cm).

The dough was baked at 180° C. for 25 to 30 minutes.

After baking, the sponge cakes were unpanned and cooled.

6. Results of the Tests

Relative volume differences of less than 3% are not relevant.

Test 1 (100 g test)

|  | Volume | % volume increase compared to reference* |
|---|---|---|
| Reference | 630 |  |
| Reference + 0.5% guar | 690 | 10 |
| Reference + 1% guar | 660 | 5 |
| Reference + 0.5% dextrans B512F | 675 | 8 |
| Reference + 1% dextrans B512F | 695 | 12 |

Test 2 (100 g test)

|  | Volume | % volume increase compared to reference* |
|---|---|---|
| Reference | 625 |  |
| Reference + 0.5% P171 dextrans | 735 | 18 |
| Reference + 1% dextrans P171 | 825 | 32 |

Test 3 (Influence of cells) (100 g test)

|  | Volume | % volume increase compared to reference* |
|---|---|---|
| Reference | 610 |  |
| Reference + 1% P171 dextrans cellfree precipitation | 775 | 27 |
| Reference + 1% P171 dextrans precipitation with cells | 750 | 23 |

Test 4
(Use of complete culture medium-expressed as dry substance)-(100 g test)

|  | Volume | % volume increase compared to reference* |
|---|---|---|
| Reference | 635 |  |
| 1% P171 | 685 | 8 |
| 2% P171 | 715 | 13 |
| 3% P171 | 805 | 27 |

Test 5: in "Belgian pistolets" together with a complete improver.

|  | Volume | % volume increase compared to reference* |
|---|---|---|
| Reference | 1700 | 0 |
| Reference + 3% S500 | 3050 |  |
| Reference + 3% S500 (without emulsifier) | 2500 |  |
| Reference +3% S500 + 1% P171 | 3375 | 10% compared to S500 |
| Reference + % S500 (without emulsifier + 1% P171) | 2850 | 14% compared to S500 (without emulsifier) |

S500 is a commercial bread improver from Puratos N.V.
*unless marked otherwise.

Test 6: Sponge Cake

The density of the sponge cakes is evaluated.
The density of the baked product is calculated based on the volume measured by the rapeseed displacement method and the weight.

Results:

|  | Tegral Biscuit | Whole eggs | Water | dextrans P171 |
|---|---|---|---|---|
| Reference | 500 g | 375 g | 50 g | 0 |
| Test A | 500 g | 375 g | 50 g | 5 g |
| Test B | 500 g | 375 g | 50 g | 10 g |

|  | Batter density | sponge cake density |
|---|---|---|
| Reference | 410 g/l | 334 g/l |
| Test A | 398 g/l | 308 g/l |
| Test B | 389 g/l | not determined |

7. Conditions of Fermentation 7.1 Classic Batch Fermentation

An inoculum was prepared, which then was inoculated in a proportion of 2–15% in the final fermentation medium. A possible composition of the fermentation medium:

sucrose 40 g/l
lab lemco 8 g/l
yeast extract 4 g/l
tween 80 ml/l
triammoniumcitrate 2 g/l
sodiumacetate.trihydrate 5 g/l
dipotassium hydrogen phosphate 2 g/l
$MgSO_4.7H_2O$ 0.2 g/l
$MnSO_4.4H_2O$ 50 mg/ml
initial pH 6.7

After a fermentation of 12–20 hours at 25° C., the inoculum was inoculated into the final fermentation medium. Then a classic batch fermentation with *Leuconostoc mesenteroides* P171 took place. The fermentation took place in a Biostat B fermentor (Braun) with a capacity of 2l. Considering the industrial application, it was decided to choose the simplest medium, made up of the following components: sucrose as C-source, yeast extract (Oxoid L21®) as complex N-source and as source for co-factors, $Na_2HPO_4$-salt as buffer.

A possible composition would be:

sucrose 125 g/l
yeast extract 20 g/l
$Na_2HPO_4$ 16 g/l
initial pH 6.7

Sucrose can vary between 50 and 400 g/L. The initial pH can vary between 7 and 6.1, and therefore, it was necessary to buffer the solution.

Buffer salts can be any chemical substance which has the capacity to buffer in the given area.

During fermentation, only the temperature was checked, there was no pH control, no aerating. Nevertheless, stirring took place to avoid heterogeneous substances in the fermentor.

The conditions in which the fermentation took place are described in the table below:

| | |
|---|---|
| temperature | 25° C. |
| volume | 1.5 l |
| aeration | no |
| agitation | 200 rpm |
| inoculum | 6.7% |

The working temperature was set to 25° C. In general, the temperature can be set between 20 and 30° C. The pH value decreases in the course of the fermentation. When the pH value no longer decreases, the fermentation has ended.

7.2 Preparation of Dextransucrase and the Consequent Synthesis of Dextrans

It was not necessary to synthesize the dextrans in presence of the micro-organism. It was possible to produce the dextransucrase first, using the adequate micro-organisms (in the present case preferably the P171). First an inoculum was prepared according to the procedure mentioned above. This inoculum was inoculated in a fermentor. A possible culture medium would be:

yeast extract 20 g/l disodium hydrogen phosphate 16 g/l sucrose 40 g/l initial pH 6.7

Afterwards, the cells were separated from the culture medium by microfiltrating or centrifuging.

If necessary, the culture medium was concentrated by ultrafiltration.

Afterwards, the enzymatic solution was diluted into a concentrated sugar solution, and the dextrans were synthesized. This dextran synthesis can also be achieved by direct addition of dextransucrase or dextrine dextranase in the basic formulation of the end product that was baked. The dextrans were then formed during fermentation.

8. Dextrans Isolation

In order to isolate the dextrans, a volume of culture medium was mixed with a same volume of ethanol (this is also possible with isopropanol). This causes the dextrans to precipitate. After precipitation of the dextrans, the supernatant was carefully skimmed.

The obtained precipitation was frozen, and afterwards lyophilized. The lyophilized dextrans were ground and used in baking tests.

Another protocol consists in diluting the culture medium first by adding dextrans. To centrifuge the solution in order to eliminate the cells and then to precipitate and dry the dextrans.

Lyophilizing can also be replaced by drying in the air, or drying at an increased temperature. Spray drying was also possible at this stage.

What is claimed is:

1. Dextrans having molecular weight exceeding $2 \times 10^6$ daltons and a branching grade lower than 5% and when subjected to a constant stress, giving a rise in viscosity of more than $0.4 \times 10^{-3}$ Pas after 5000 seconds for a 1% solution of dextrans in water with a stress of 0.5 Pa.

2. The dextrans according to claim 1, having a proton-nuclear magnetic resonance (1H-NMR) spectrum with a resonance duplet at $\delta 4.99$ ppm and $\delta 4.97$ ppm and a less pronounced resonance at $\delta 5.32$–5.30 ppm.

3. The dextrans according to claim 1, wherein the dextrans are lyophilized.

4. The dextrans according to claim 1, wherein said dextrans are produced from a micro-organism strain deposited in the Belgian Coordinated Collection of Micro-Organisms (BCCM) under accession number LMGP-16878.

5. Dough comprising dextrans according to claim 1.

6. A baked food product produced by baking the dough of claim 5.

* * * * *